United States Patent
Naik et al.

(10) Patent No.: US 12,417,839 B2
(45) Date of Patent: Sep. 16, 2025

(54) ARTIFICIAL INTELLIGENCE (AI)-BASED OPTIMIZED SOLUTION FOR DEVICE LOCALIZATION IN MEDICAL FACILITY SET-UP

(71) Applicant: KONINKLIJKE PHILIPS N.V., Eindhoven (NL)

(72) Inventors: Sarif Kumar Naik, Bangalore (IN); Ravindra Patil, Bangalore (IN); Karthick Raja, Bangalore (IN); Shraddha Barodia, Bangalore (IN); Sampad Kumar Mohanty, Bangalore (IN); Rose Ramasamy, Vriddhachalam (IN); Meru Adagouda Patil, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 260 days.

(21) Appl. No.: 18/037,790

(22) PCT Filed: Nov. 18, 2021

(86) PCT No.: PCT/EP2021/082054
§ 371 (c)(1),
(2) Date: May 19, 2023

(87) PCT Pub. No.: WO2022/106500
PCT Pub. Date: May 27, 2022

(65) Prior Publication Data
US 2024/0006064 A1    Jan. 4, 2024

Related U.S. Application Data

(60) Provisional application No. 63/116,950, filed on Nov. 23, 2020.

(51) Int. Cl.
G16H 40/40    (2018.01)
G06T 19/00    (2011.01)
G16H 40/20    (2018.01)

(52) U.S. Cl.
CPC .......... *G16H 40/40* (2018.01); *G06T 19/006* (2013.01); *G16H 40/20* (2018.01); *G06T 2210/04* (2013.01); *G06T 2219/004* (2013.01)

(58) Field of Classification Search
None
See application file for complete search history.

(56) References Cited

U.S. PATENT DOCUMENTS 8,830,267 B2    9/2014 Brackney
10,825,566 B1 * 11/2020 Maissy .................. A61B 6/566
(Continued)

FOREIGN PATENT DOCUMENTS

WO    2018/158347 A1    9/2018

OTHER PUBLICATIONS

International Search Report and Written Opinion Dated Mar. 1, 2022 For International Application No. PCT/EP2021/082054 filed Nov. 18, 2021.

*Primary Examiner* — Hilina K Demeter

(57) ABSTRACT

A method (100) of determining a layout for one or more medical devices (12) in a medical facility includes: obtaining images (30) of a plurality of locations of the medical facility; mapping the obtained images to an architectural layout of the medical facility; generating a three-dimensional (3D) model of the medical facility based on the mapping; determining a recommended location for the one or more medical devices using the 3D model; determining a recommended placement of the one or more medical devices in the recommended location based on the recommended location; and outputting an image (40) showing the deter- (Continued)

mined recommended placement of the medical devices in the recommended location.

16 Claims, 6 Drawing Sheets

(56) References Cited

U.S. PATENT DOCUMENTS

| | | | | |
|---|---|---|---|---|
| 2008/0059120 A1* | 3/2008 | Xiao | ............... | G06F 11/0748 |
| | | | | 702/187 |
| 2010/0138238 A1* | 6/2010 | Sobie | ............... | G16H 10/60 |
| | | | | 705/2 |
| 2013/0304489 A1* | 11/2013 | Miller | ............... | G06Q 10/20 |
| | | | | 705/2 |
| 2016/0378887 A1 | 12/2016 | Maldonado | | |
| 2017/0231573 A1* | 8/2017 | Reiner | ............... | A61B 5/6861 |
| 2018/0247024 A1* | 8/2018 | Divine | ............... | G16H 40/20 |
| 2019/0041972 A1 | 2/2019 | Bae | | |
| 2019/0180433 A1* | 6/2019 | Sasson | ............... | G06V 20/176 |
| 2020/0120308 A1* | 4/2020 | McMillan | ............... | G06F 3/017 |
| 2020/0395118 A1* | 12/2020 | Codd | ............... | G16H 40/40 |

* cited by examiner

ARTIFICIAL INTELLIGENCE (AI)-BASED OPTIMIZED SOLUTION FOR DEVICE LOCALIZATION IN MEDICAL FACILITY SET-UP

CROSS REFERENCE TO RELATED APPLICATIONS

This application is the U.S. National Phase application under 35 U.S.C. § 371 of International Application No. PCT/EP2021/082054 filed Nov. 18, 2021, which claims the benefit of U.S. Provisional Patent Application No. 63/116,950 filed Nov. 23, 2020. These applications are hereby incorporated by reference herein.

FIELD

The following relates generally to the medical device arts, medical device installation arts, hospital ergonomics arts, artificial intelligence (AI) arts, augmented reality (AR) arts, multi-criteria optimization arts, and related arts.

BACKGROUND

Installation of medical devices, such as a magnetic resonance imaging (MRI) device, computed tomography (CT) device, positron emission tomography (PET) scanner, radiation therapy (RT) device, X-ray systems, laboratory testing equipment, or other medical devices is a complex task. An important factor in the installation is selecting the location and placement of the medical device. For example, an MRI device requires structural support including a solid structural foundation to dampen vibrations, extensive electrical and water power feeds, ancillary cryogenic fluid handling (for MRI devices employing a cryogenic magnet), and radiofrequency (RF) shielding (usually the MRI is placed in an MRI room with RF-shielded walls, ceiling, and flooring forming a Faraday cage). A RT device or PET scanner requires many similar considerations as well as provisions for handing radioactive agents. In addition to electrical, water, and other ancillary systems, the use of a medical device for critical patient care can impose further locational and placement limitations. For example, it may be desirable for an MRI device to be placed close to the emergency room or other hospital department(s) that handle critically ill patients requiring MRI examinations. Within the location, the placement of the medical device should provide medical personnel with access to all requisite working areas and allow for sharing of the same device by one or more departments or personnel. As yet a further consideration, various governmental regulations may impact permissible locations and placements of the medical device.

The installation of an MRI, PET, RT, or other large, complex medical device is an expensive and lengthy process. Electrical, water, and other infrastructure installation, and transport of the medical device to the location and placement in that location take considerable time and may adversely impact hospital operations. Consequently, it is undesirable (and in some cases impossible) to re-locate and/or re-position the medical device after installation if it is subsequently discovered that the location and/or placement of the medical device is less than ideal.

The selection of the location and placement of the medical device is typically jointly determined by the vendor of the medical device and by the customer (e.g. a hospital) leasing or purchasing the medical device. The vendor has specialized knowledge as to the requirement of the medical device and its ancillary infrastructure. By contrast, hospital representatives have specialized knowledge of hospital operations and the intended functionality of the medical device. The vendor and the customer may have different but complementary knowledge of applicable governmental regulations. Both the knowledge base of the vendor and the knowledge base of the customer are of importance in selecting the optimal location and placement of a new or expanded medical device. However, it can be difficult for vendor and hospital representatives to work together to combine their respective knowledge bases in order to jointly select the best location and placement of the medical device. This is especially the case if the vendor and customer are in different states, countries, or even continents.

A criterion for any hospital management team is how effectively and efficiently the setup of the medical facility is running. Hence, it very important to plan positions and placements of medical devices in the medical facility during initial setup as well as when expansion takes place. In a medical facility, there are various imaging and diagnostic devices are required to be installed based on the medical facility units/departments or kind of care the medical facility provides like radiology, cardiac, gynecology, emergency, outpatient, etc. Additionally, the medical facility needs to have a proper planning to position these devices along with the departments. Therefore, medical facility needs find the best place to install these devices considering various factors such as current position of the department, available space inside the medical facility premise, easy accessibility to the device from all medical facility units who needs the device, smooth movement of the patients, and so forth.

For a smooth patient flow/movement in the examination room, the positioning of the medical device is an important factor given the direction entry and exit, available space in the examination room enclosure, and other peripheral devices in the enclosure. Achieving all these goals with an optimal cost is a challenging task to accomplish.

The following discloses certain improvements to overcome these problems and others.

SUMMARY

In one aspect, a non-transitory computer readable medium stores instructions executable by at least one electronic processor to perform a method of determining a layout for one or more medical devices in a medical facility. The method includes: obtaining images of a plurality of locations of the medical facility; mapping the obtained images to an architectural layout of the medical facility; generating a three-dimensional (3D) model of the medical facility based on the mapping; determining a recommended location for the one or more medical devices using the 3D model; determining a recommended placement of the one or more medical devices in the recommended location based on the recommended location; and outputting an image showing the determined recommended placement of the medical devices in the recommended location.

In another aspect, an apparatus for determining a layout for one or more medical devices in a medical facility includes an augmented reality (AR) headset comprising a stereo camera configured to obtain images of a plurality of locations of the medical facility. At least one electronic processor is programmed to: map the obtained images to an architectural layout of the medical facility; generate a 3D model of the medical facility based on the mapping; determine a recommended location for the one or more medical devices using the 3D model; determine a recommended placement of the one or more medical devices in the recommended location based on the recommended location; and output an image showing the determined recommended placement of the medical devices in the recommended location.

In another aspect, a method of determining a layout for one or more medical devices in a medical facility includes: obtaining images of a plurality of locations of the medical facility; mapping the obtained images to an architectural layout of the medical facility; generating a 3D model of the medical facility based on the mapping; performing a multi-agent optimization on the 3D model in which each agent of the multi-agent optimization optimizes for a corresponding feature; determining a recommended location for the one or more medical devices based on the multi-agent optimization; determining a recommended placement of the one or more medical devices in the recommended location based on the recommended location; and outputting an image showing the determined recommended placement of the medical devices in the recommended location.

One advantage resides in identifying an optimized location and placement for a medical device inside of a medical facility.

Another advantage resides in improved medical facility management and throughput.

Another advantage resides in providing for improved movement and traffic flow through a medical facility to and from a newly installed or expanded medical device.

Another advantage resides in optimizing costs in time and energy for caregivers utilizing a newly installed or expanded medical device in the medical facility.

Another advantage resides in improved cost-effective management of resources in the medical facility.

Another advantage resides in identifying a best position inside a designated enclosure suggesting a positioning of all medical devices to be installed in a medical facility.

Another advantage resides in improved patient movement through the medical facility.

Another advantage resides in improved turnaround for medical examinations.

Another advantage resides in providing a tool for selecting the location and placement of a medical device which facilitates combining the knowledge bases of the medical device vendor and the customer (e.g., hospital) along with consideration of any applicable governmental regulations in order to identify a best location and placement of the medical device in a specific hospital.

Another advantage resides in quick and convenient access of medical devices to technician and doctors, thereby reducing stress and helping patients with better care.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
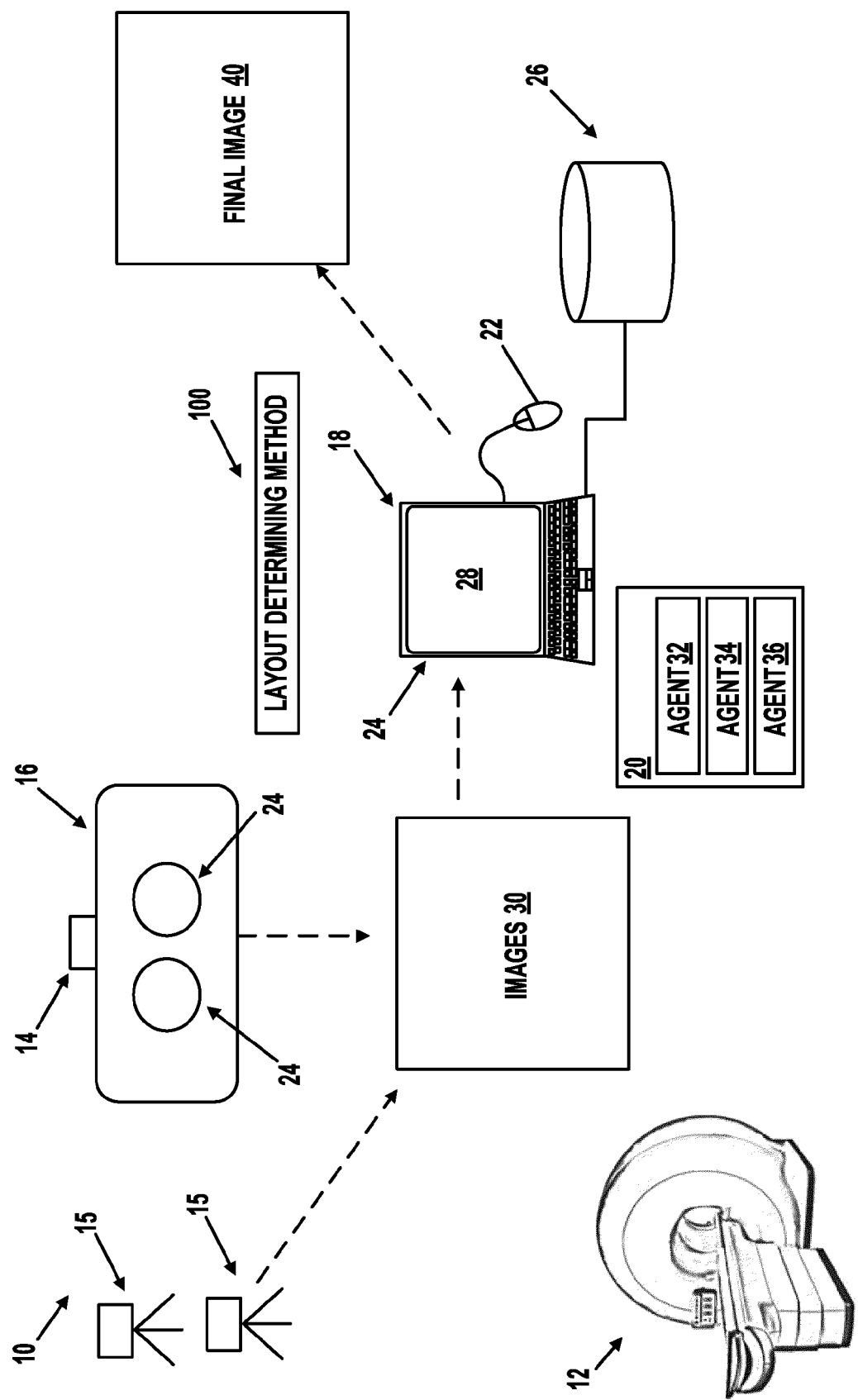
FIG. 1 diagrammatically illustrates an illustrative system for determining a layout for one or more medical devices in accordance with the present disclosure.

The placement of a magnetic resonance imaging (MRI) device, or other medical devices is an important part of deployment of the device. Improper placement can substantially degrade workflow efficiency and can adversely impact usability of the device. Moreover, due to the high cost of the installation, both in monetary terms and in terms of adverse impact on hospital operations, a non-optimal location and/or placement of the medical device may be difficult or impossible to remedy after the installation.

An approach disclosed herein for optimizing the location and placement of a medical device employs images of the rooms, hallways, and other spaces of the hospital. The imaging is done using an augmented reality (AR) headset, possibly also including virtual reality (VR) capability. Using an AR headset for collecting the imaging data advantageously enables the wearer to annotate landmarks during the image acquisition, such as labeling instruments, doors, and so forth. The outside of the building may also be similarly mapped using a camera-equipped aerial drone.

The acquired images are mapped to a building architectural plan using the labeled landmarks to align the images with corresponding features in the plan and thereby create a three-dimensional (3D) model of the hospital. Similarly, other building layouts that may be available, such as a plumbing layout, electrical layout, et cetera, can be mapped to the 3D model.

Next, the optimal location for the MRI (or other medical device) is determined using the 3D model. The optimal location is defined at the room level (i.e., the optimal location will be a specific room). In some embodiments, a multi-agent optimization is used, in which each agent optimizes for a specific feature. There may, for example, be: an agent to minimize distance from the location to the emergency room (ER); an agent to minimize the number of elevator trips between the ER and the location; an agent to minimize distance from the location to the nearest emergency exit; and so forth. Other constraints may be employed, e.g. minimum room size. The impact of the agents may be weighted in the multi-agent optimization, and agents may share information. This provides a formalism for taking into account a wide range of customer-specific considerations in a flexible manner. Advantageously, the multi-agent optimization can employ agents implementing features to be optimized which are specified by the customer who is purchasing or leasing the medical device, and also agents implementing features to be optimized which are specified by the vendor of the medical device. This efficiently combines considerations generated by the respective knowledge bases of the customer and vendor.

Once the optimal location is determined, a position/orientation optimization is performed to optimize the position and orientation of the MRI (or other medical device) in the optimal location (i.e. optimal room). Various constraints imposed by government regulations and/or manufacturer specifications can be applied, such as a minimum distance from walls, minimum lighting specifications, or so forth. These constraints can be customer-specific. For example, standard sets of constraints may be provided for various countries or regions such as the United States, the European Union, China, Japan, and/or so forth, and the appropriate set of constraints for the location of the customer are then selected and applied. As the room has been chosen, this position/orientation (more generally, placement) optimization can in some cases employ a brute-force grid optimization in which a grid of possible position/orientation combinations is searched to identify the position/orientation that meets all constraints and minimizes an optimization function. Other approaches such as applying a machine learning component trained on, for example, historical MRI installations with the optimal position/orientation labeled is also contemplated.

As part of the position/orientation (more generally, placement) optimization or as a separate subsequent step, a validation is performed to ensure that the chosen position/orientation satisfies various governmental, manufacturer, customer, or other regulations and/or specifications.

In some embodiments disclosed herein, the process can possibly be iterative, e.g. if the location optimization selects a room but the position/orientation optimization cannot find an acceptable position/orientation in that room then flow may return to the location optimization which is rerun with the additional constraint that the originally selected room is now excluded. Likewise, if the validation fails then flow may return to the position/orientation optimization with the originally chosen position/orientation now excluded.

The process is in some embodiments mostly automated, except for the collecting of images using the AR headset and optional drone. A graphical user interface (GUI) may be provided, which displays the various steps and may allow for user interaction. For example, the initially generated 3D map may be displayed, with landmarks labeled, and the user can elect to adjust the landmarks. After completion of the location optimization the 3D map is again shown with the selected room highlighted, optionally along with highlighting other features optimized by the various agents such as highlighting the path between the selected room and the ER. After the position/orientation optimization is run, a "zoomed" 3D image of the selected room with the medical device at the proposed position/orientation is shown. If any validation criterion failed, this may also be highlighted on the display of the medical device in the room. The user may then select to re-run the location and/or placement optimization in view of the failed validation criterion, or may (at least tentatively) accept the recommended location and/or placement with the intent to seek a governmental variance for the failed validation criterion or to determine some other remediation of the failed validation criterion.

In some embodiments, instances of the GUI are provided at both vendor and customer locations via the Internet, so that a vendor representative and a customer representative can view the display of the various steps simultaneously. In combination with video conferencing built into the GUI or provided as a separate application running in a separate window on the respective vendor and customer computers, this can enable the vendor and customer to collaborate in real time in designing and planning the location and placement of the medical device. In one approach, the customer GUI instance provides read-only access for the customer, while the vendor GUI instance provides both viewing and control capabilities. This allows a single actor (the vendor) to control the optimization process, in videoconference consultation with the customer. Alternatively, the customer may also be provided with some or all optimization control capabilities. Such an approach advantageously provides real-time vendor-and-customer collaborative planning of the location and placement of the medical device, even in cases where the vendor and customer are located in different countries or continents.

An advantage of the location optimization using multi-agent optimization is that it enables a wide range of customer-specific and/or vendor-specific considerations to be taken into account in a flexible manner. This provides an efficient way to merge customer and vendor knowledge as to the features that should be optimized in the location and placement of the medical device. Another advantage of the disclosed process is that it is readily extended to optimal placement of multiple medical devices of the same or different types (e.g. two MRI machines, or an MRI machine and a CT machine). To do so, the multi-agent optimization includes agents for optimizing the placement of each medical device. As the agents can optionally share information, this can ensure that interdependencies of the placements of the two medical devices can be taken into account. Once, each medical device is placed in its room, the subsequent position/orientation optimization and validation steps are performed independently and individually for each respective medical device.

With reference to FIG. 1, an illustrative apparatus or system 10 for determining an optimal location and placement for one or more medical devices 12 (e.g., an MRI device or other imaging modality device) in a hospital or other medical facility is shown. To do so, the apparatus 10 includes a stereo camera 14 configured to acquire stereo images or videos of locations of structures within a medical facility. The stereo camera 14 typically includes multiple lenses or lens assemblies with a separate sensor for each lens that forms an image on a digital detector array (e.g. a CCD imaging array, a CMOS imaging array, et cetera) to capture 3D images. The stereo camera 14 preferably has color video capability, e.g. by having an imaging array with pixels sensitive to red, green, and blue light (or another set of colors substantially spanning the visible spectrum, e.g. 400-700 nm). The stereo camera 14 optionally may include other typical features, such as depth detection, a built-in flash (not shown) and/or an ambient light sensor (not shown) for setting exposure times.

FIG. 1 also shows an electronic processing device 18, such as a workstation computer, a smartphone, a tablet, or so forth. Additionally or alternatively, the electronic processing device 18 can be embodied as a server computer or a plurality of server computers, e.g. interconnected to form a server cluster, cloud computing resource, or so forth. In other embodiments, the electronic processing device 18 can be integrated into an augmented reality heads-up (AR-HUD) device 16.

The electronic processing device 18 includes typical components, such as an electronic processor 20 (e.g., a microprocessor), at least one user input device (e.g., a mouse, a keyboard, a trackball, and/or the like) 22, and at least one display device 24 (e.g. an LCD display, an OLED display, a touch-sensitive display, plasma display, cathode ray tube display, and/or so forth). In some embodiments, the display device 24 can be a separate component from the electronic processing device 18. The display device 24 may also comprise two or more display devices.

The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the electronic processing device 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the display device 24.

In some embodiments, the stereo camera 14 comprises the AR-HUD device 16 with one or more AR-HUD displays comprising the display device (s) 24. The illustrative design employs left-eye and right-eye displays 24, but alternatively the display can be a single large window that spans both eyes. In some examples, the stereo camera 14 is mounted to the AR-HUD device 16 to provide a "first person view" so as to align the AR content with the actual view seen through the transparent display(s) 24 of the AR-HUD. In some examples, the AR-HUD device 16 can be configured as a helmet, a headband, glasses, goggles, or other suitable embodiment in order to be worn on the head of the user. The stereo camera 14 is mounted to the AR-HUD device 16 (e.g., to overlay the user's forehead, or including two stereo cameras disposed on lenses of the glasses). In other embodiments, the stereo camera 14 can comprise, or be mounted to, one or more drone devices 15 configured to obtain images of an exterior of the medical facility.

Figure 2:
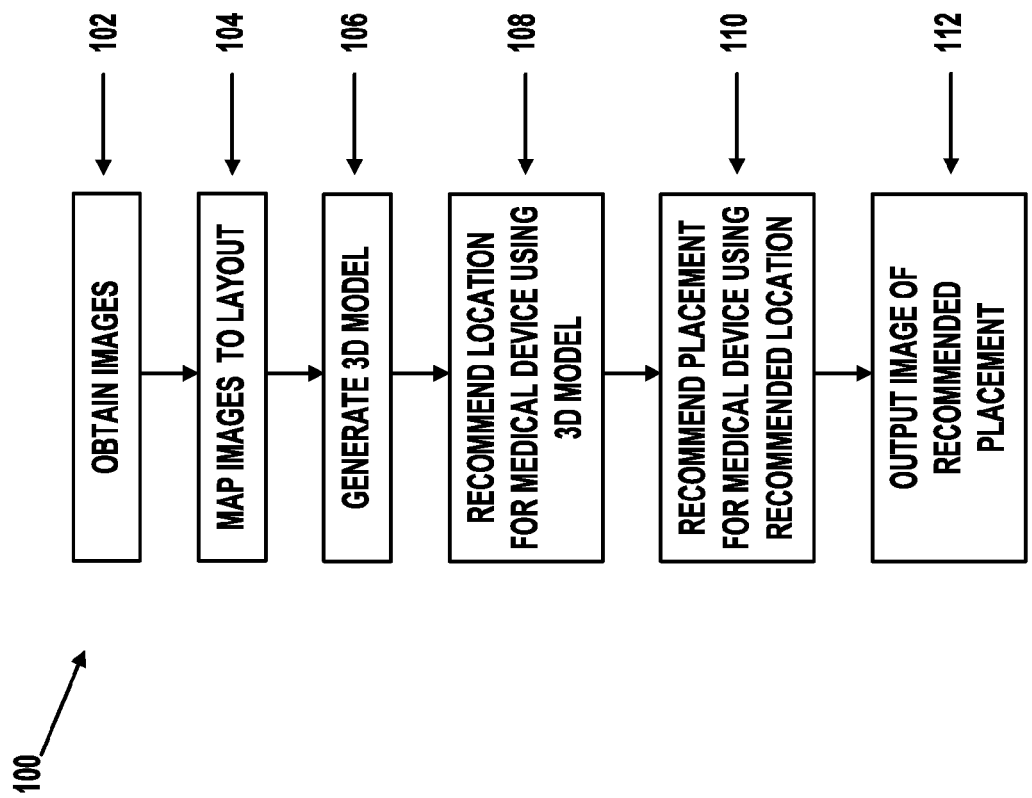
FIG. 2 shows exemplary flow chart operations of the system of FIG. 1.

Furthermore, as disclosed herein, the non-transitory storage media 26 performs a method or process 100 for determining a layout for one or more medical devices 12 in the medical facility. With reference to FIG. 2, and with continuing reference to FIG. 1, the electronic processing device 18 is configured as described above to perform the method 100 for determining a layout for one or more medical devices 12 in the medical facility 2. The non-transitory storage medium 26 stores instructions which are readable and executable by the electronic processing device 18 to perform disclosed operations including performing the method or process 100. In some examples, the method 100 may be performed at least in part by cloud processing.

In some embodiments, the apparatus 10 can be implemented using the AR-HUD device 16 (and optionally the drone devices 15) to acquire images of the interior and exterior of the medical facility, and the electronic processing device 18 can be embodied as a workstation computer (or tablet) which processes the acquired images to determine the layout for the medical device 12 (and can optionally receive user inputs from the user via the at least one user input device 22 to edit the acquired images). In other embodiments, the electronic processing device 18 can be implemented in the AR-HUD device 16, in which case the at least one user input device 22 comprises a touch-sensitive screen on the display devices 24 in which the user can "finger tap" portions of the displayed images.

At an operation 102, images 30 of a plurality of locations in the medical facility are obtained. In some embodiments, images 30 of the interior of the medical facility are obtained by the AR-HUD device 16 (and can be used to obtain images of the exterior of the medical facility). In other embodiments, the drone devices 15 are used to obtain images of the exterior of the medical facility.

At an operation 104, the obtained images 30 are mapped to an architectural layout of the medical facility. The architectural layout of the medical facility can include, for example, electrical diagrams, plumbing diagrams, walls, floors, roof, corners, bathrooms, pipes, switches position, rooms, hallways, and so forth. In some embodiments, the mapping operation 104 includes receiving annotations from a user via the at least one user input device 22 (e.g., fingertips). The annotations can comprise labels of landmarks (e.g., walls, switches, pipes, and so forth) included in the obtained images 30. The annotated landmarks are mapped to the architectural layout of the medical facility.

At an operation 106, a three-dimensional (3D) model of the medical facility is generated based on the mapping process. In some embodiments, the modelling operation 106 includes providing the GUI 28 on the display device 24. Inputs from the user are received via the at least one user input device 22. The inputs are indicative of a labelling or adjustment of landmarks in the obtained images 30.

At an operation 108, a recommended location for the one or more medical devices 12 is determined using the 3D model. To do so, a multi-agent optimization implemented by the at least one electronic processor 20 is performed on the 3D model, in which each agent of the multi-agent optimization optimizes for a corresponding feature in the 3D model. The recommended location is then determined based on the multi-agent optimization process. The agents of the multi-agent optimization can include, for example, an agent 32 to minimize a distance between the recommended location and an emergency room (ER), an agent 34 to minimize a number of elevator trips between the recommended location and the ER, an agent 36 to minimize a distance between from the recommended location and a nearest emergency exit, and so forth. A weighted average of outputs puts of these agents are then optimized to determine the recommended location for the one or more medical devices 12. In some examples, image representations of the optimized agents generated by the performed multi-agent optimization can be displayed on the display devices 24.

At an operation 110, a recommended placement of the one or more medical devices 12 in the recommended location is determined based on the recommended location. As used herein, the term "placement" refers to both a position and an orientation of the medical device 12. In some embodiments, the recommended placement of the medical device(s) 12 can be determined based on constraints (e.g., building constraints, manufacturing constraints, government constraints, and so forth) of the medical facility. To do so, a grid optimization processor is performed to identify the position and/or orientation of the one or more medical devices 12 that satisfies the constraints. In other embodiments, the recommended placement of the medical device(s) 12 is determined using a machine-learning process trained on historical installations of the one or more medical devices to determine the position or orientation for the medical device(s).

In some embodiments, the recommended placement operation 110 can include validating the recommended location or the recommended placement of the one or more medical devices 12 to ensure the recommended location or the recommended placement satisfies manufacturing, building, or government regulations related to the medical facility. The determining of the recommended location or the recommended placement of the one or more medical devices 12 can be repeated when one or more of the regulations is not satisfied.

At an operation 112, a final image 40 is output showing the determined recommended placement of the medical device(s) 12 in the recommended location. The final image 40 can be displayed on the display device 24. In some embodiments, the user can highlight portions of the final image 40 related to the recommended placement via the at least one user input device 22. In some embodiments, the operations 108 and/or 110 can consider multiple locations in the medical facility, including rooms that are currently fitted for other equipment. In these embodiments, the final image 40 can show the existing medical devices or equipment as being removed, and replaced with the proposed new equipment. In some examples, a recommendation can be output for the location of any displaced medical device or equipment. The location recommendations can then be feed into a cost calculator (implemented in the electronic processing device 18) so that the locations and re-locations can take into account construction costs, installation costs and de-installation costs.

Although described above in terms of the single medical device 12, the operations 102-112 of the method 100 can be repeated for any number of medical devices to be installed in the medical facility.

EXAMPLE

Figure 3:
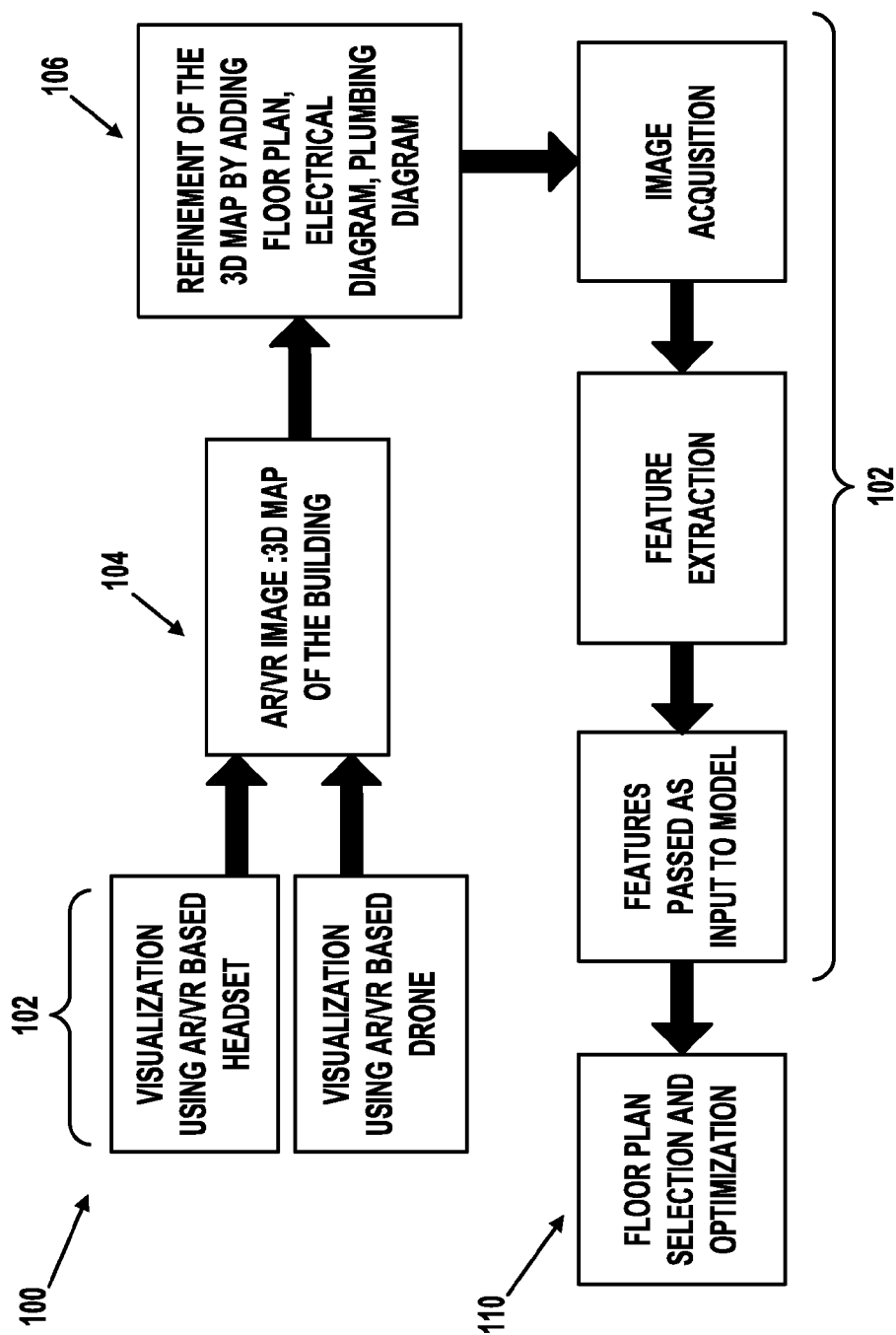
FIGS. 3-6 diagrammatically illustrate further illustrative embodiments of the flow chart shown in FIG. 2.

The following describes an example implementation of the method 100, another embodiment of which is illustrated in FIG. 3. At the imaging operation 102, the images 30 of the medical facility are obtained by the AR-HUD device 16 and/or the drone devices 15. At the mapping operation 104, the architectural layout of the medical facility is mapped to the images 30 using any suitable mapping algorithm.

The modeling operation 106 generates the 3D model of the medical facility, which is input to the multi-agent optimization process at the operation 108. The multi-agent optimization process is configured to identify all the relevant structures within the medical facility, such as the hallway size, position of the doors, stairs, windows existing infrastructure etc. To do so, the multi-agent optimization process extract multiple features from the 3D model, including an Interest Point Detection (IPD) feature (that is based on the generated scaled response maps in which the maxima and minima are detected and used as the Interest Points); an Orientation Assignment (OA) feature (in which each detected Interest Point is assigned a reproducible orientation to provide rotation invariance (i.e., invariance to image rotation); a Descriptor Extraction (DE) feature (in which an interest point is uniquely identified such that it is distinguished from other interest points such as doors, windows, passages), among others. Features such as like walls, corners, distance to the device, switches position etc., can be extracted.

The multi-agent optimization process includes multiple agents working on multiple characteristics of movement from one place to other. For example, a first agent 32 can determine the time taken to travel from point A to point B. A second agent 34 can determine the number of steps, bends on the path from A to B, a third agent 36 to determine a distance between from Point A or B and a nearest emergency exit, and so forth. Each agent has its own utility function to estimate the cost to travel from point A to B. The cost will be different for each of the agent. The parameters of the agent(s) are adjusted such that the overall cost of movement in the medical facility can be reduced.

The multi-agent optimization process can be expressed as Equation 1:

$$\text{min Total cost} = \sum_{i=1}^{n}\sum_{j=1}^{n}\sum_{k=1}^{n}\sum_{l=1}^{n} f_{ik}\, c_{ikl} d_{jk}\, x_{ij}$$

-continued

Subject to $\sum_{k=1}^{n} x_{ij} = 1$ for $j = 1, 2, 3, \ldots, n$ $\sum_{j=1}^{n} x_{ij} = 1$ for $j = 1, 2, 3, \ldots, n$ $x_{ij} \in \{0, 1\}$ for $i, j = 1, 2, 3, \ldots, n$ where $C_{ik}$ is the transportation cost for unit object for unit distance between place i and j; $f_{ik}$ is the number of people/other object flow from facility i to k; $d_{jk}$ is the distance between the facility j and k; and $x_{ij}=1$ if the facility i is assigned to j and $x_{ij}=0$ if the facility is not assigned to j.

The objective is to minimize the total cost of travel between the facilities to that proposed device location. The constraints help to assign only one facility is assigned to each location and only one location is chosen by each facility. An agent helps in taking an action, based on its observation of the environment. The environment could be passing information real-time to agent using sensors, or event it could be a simulated reality. The action taken by the agents have impact on the environment, changing the state of the environment. For example, when an agent decides to locate a machinery to a particular space, then the space will be no longer available to other agents. The multi-agent systems consist of non-centralized mutually co-operating agents acting autonomously.

In single agent systems, an agent will be uncertain about the effect of its action on the environment and it will have to take uncertainty into account in its decision-making process. While in multi agent systems, a single agent has to take into account of the decision made by the other systems as well. Hence in multi agent systems the agents exchange information and knowledge to get desired output which works better than single independent agents, which is considered in this scenario.

To update the parameters of these agents Q learning is used, which help to make changes to the parameters based on the objective function according to Equation 2.

$$Q^*(S_t, a_t) = Q(S_t, a_t) + b(r_{t+1} + \Upsilon \Sigma(\max a\, Q(S_t, a)) - Q(S_t, a_t)$$

where Q is the learned action-value function, and Q* is the optimal value function irrespective of the policy followed by agents. Here, this Q function will be the cost of travel based on the attribute considered by the agent. Features and Variables considered for the optimization problem are listed below in Table 1

TABLE 1

| Variable | Explanation |
| --- | --- |
| Device type (DT) | US, MR, etc. |
| Movable device | Yes/No |
| Frequency of visit I patients | Numeric, Patients: admitted as well as OPD |
| Frequency of visit I non-patients | Numeric, doctor and care takers |
| Number of patient visits | Total amount of patient flow |
| Number of non-patient visits | Total amount of non-patient flow |
| Number of blocks, bends | Total number of difficult terrain noticed by agent |
| Number of lifts | Consider both trolley and non-trolley lifts |
| Distance from Emergency wards | Emergency patients may require more care |
| Distance from OPD | There might a greater number of OPD patients |
| Distance from emergency exits | If there is a tie, emergency exist can be a decider for agents |

TABLE 1-continued

| Variable | Explanation |
| --- | --- |
| Constraints from stakeholders | Hospital might need concentration of resources at a single point/room |
| Access of bystanders | To avoid threat of AI attacks from malicious programs |

This would optimally find the location within the hospital premise where exactly the device needs to be installed in an objective fashion by considering all the necessary parameters.

Figure 4:
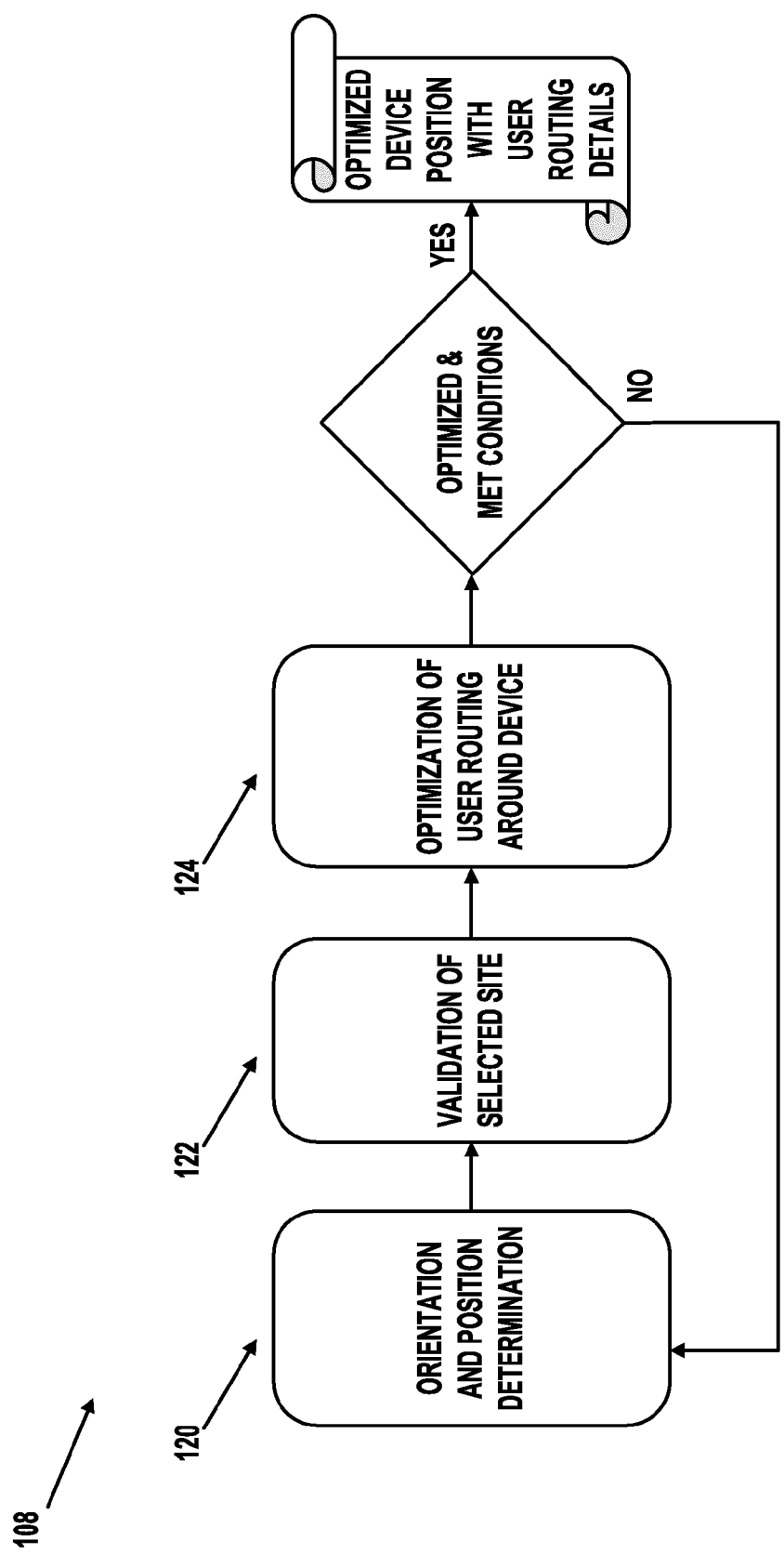

As shown in FIG. 4, the operation 108 includes using a best fit device position in a location (BFDPL) algorithm to decide a best position of the medical device 12 inside a given location, and to validate if a given location is sufficient for optimal operation of the medical device (including servicing). This algorithm has three major parts components: an orientation and position determination process 120, a validation of a selected site process 122, and an optimization of a user routing around the device process 124, each of which is described in more detail below. The BFDPL algorithm iterates the above steps one or more times and determines if given location meets original equipment manufacturer (OEM)/regulatory requirement and if the given position is optimal in all aspects, only then it ends with location and orientation of the device or message as what is causing failure to meet the requirement.

For the orientation and position determination process, four major attributes for proper positioning and orientation of the medical device 12 are factored to provide optimum performance are. These attributes can include architecture of the location, lighting, power sources and heating, ventilating and air conditioning (HVAC). Each of these elements are described in more detail below.

The architecture attribute can include features such as doorways, hallways, etc, being wide enough to ensure the system's transport to the exam room; sequence and positioning of doors, windows, walls and couch must not limit the movement of patient and the medical device 12 should be located away from door; all scan rooms should be designed to accommodate patients with disabilities as well as space for the transfer of patients from, for example, a stretcher or wheel chair to the diagnostic equipment; the medical device 12 should be positioned in an area where there is access to all sides of the patient, as well as to the other tools and devices needed for the scan; sufficient space for vertical height adjustment; repositioning should not be limited by the exam bed or device being positioned close to obstructions such as walls; areas where floor trenching is required to receive equipment infrastructure; enough space around the device for free movement of staff and patient; provision for appropriate structural shielding wherever needed can be possible; provision for proper isolation walls as appropriate for given device needs; sufficient space for a fully adjustable monitor on a monitor arm, which is detached from the main console, which can be easily positioned for both sitting and standing postures and for a variety of procedures and allow a keyboard should move independently of the monitor; among others.

The lighting attribute can include features such as: direct light on monitor should be avoided for adequate readings and display; a room should have adequate light fixtures (artificial light can be preferred over window for ambient light control), such as dim control, room darkening adjustments and variable positioning of lit area; for a special procedure and image-guided interventional rooms, fixed or mobile procedure lighting may also be required; among others.

The power source attribute can include features such as: a need for proper voltage and frequency should be supplemented by other power quality concerns, including source and load compatibility; adequate power supply plug/adaptors to support repositioning of the medical device 12; a mechanism needed to address distortion of voltage and current waveforms by harmonics present in the power systems; an option needed for reduction of potential sources of inference like application of power conditioning equipment; an option for supply of multiple power supplies like from main source, uninterruptible power supplies is needed, among others.

The HVAC attribute can include features such as: all equipment/exam rooms should have positive air pressure with respect to the adjoining areas to help maintain a reduced dust environment for the electronic equipment; air conditioning systems should be provided to heat, cool and ventilate the individual spaces, as required to satisfy the design criteria; adequate ventilation for medical gas and heat; a design of the area must also provide adequate venting in the event that a superconducting magnet should quench; a room should not be damp or subjected to extreme of temperature, among others.

Figure 5:
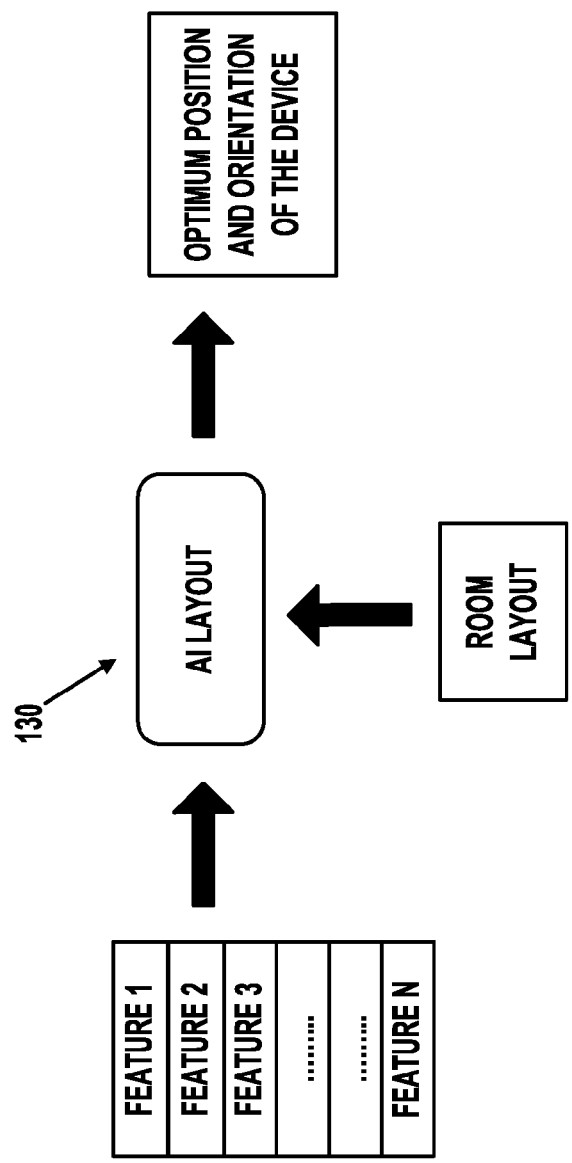
Figure 6:
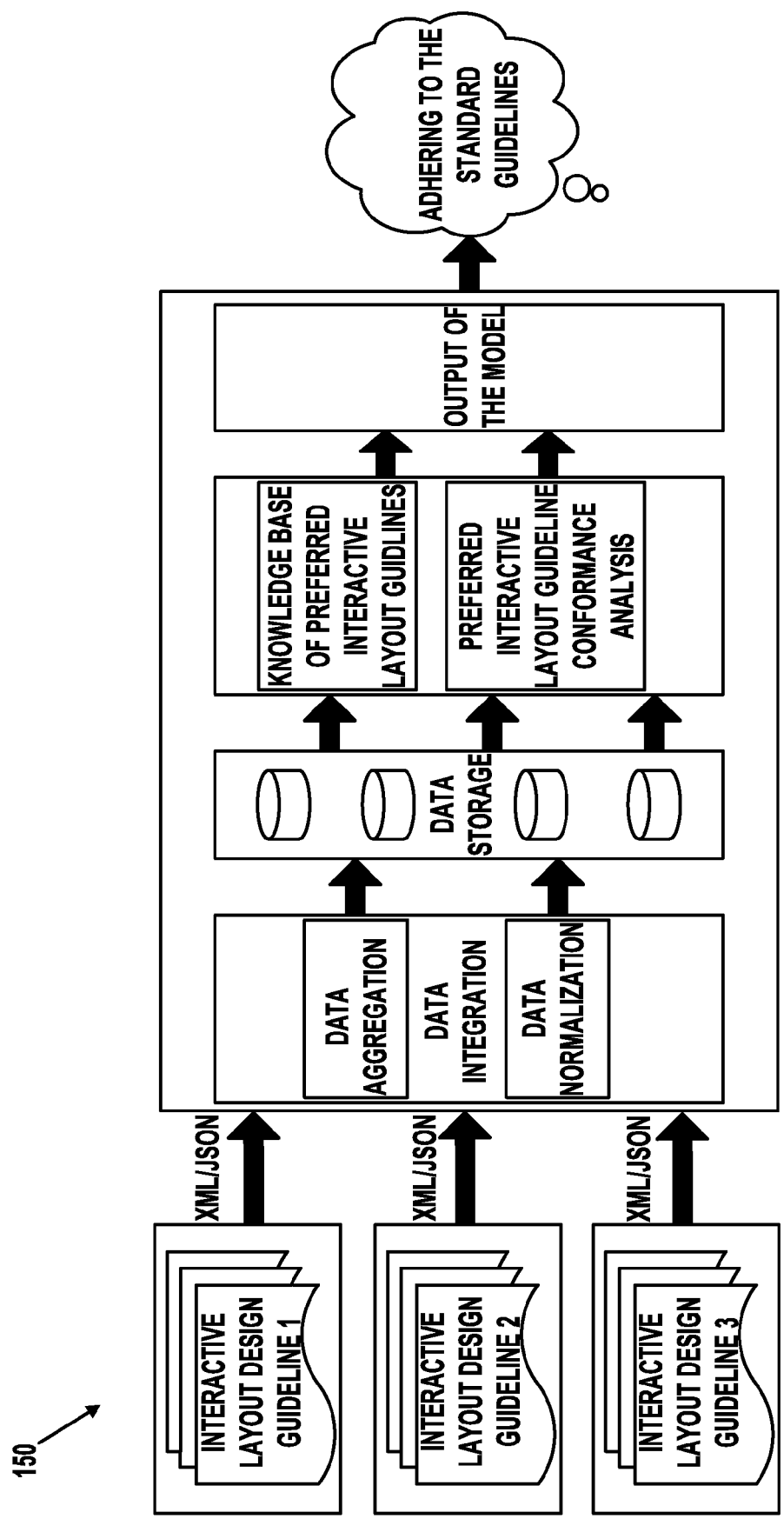

These attributes can be input into an AI model 130, as shown in FIG. 5. The model 130 can then pick the most optimum position and orientation as per the layout for the given room. Table 2 summarizes the features of the attributes.

TABLE 2

| Feature | Description |
| --- | --- |
| Feature 1 | Access to all sides of the patient |
| Feature 2 | Adequate Access of support tools, probes, monitor, keyboard, and power supply. |
| Feature 3 | Space to allow independent movement of keyboard and monitor |
| Feature 4 | Space for horizontal and vertical repositioning |
| Feature 5 | Space to accommodate patients with disabilities as well as space for the transfer of patients from a stretcher to the diagnostic equipment. |
| Feature 6 | Access to all sides of the device for possible repair/component replacement |
| Feature 7 | Appropriate structural shielding requirement |
| Feature 8 | Configuration of framing systems to accommodate support and serviceability requirements established by the manufacturer |
| Feature 9 | adequate light fixtures (mobile and fixed) |
| Feature 10 | Device positioning away from door and window |
| Feature 11 | Voltage and frequency requirements/power conditioning requirement |
| Feature 12 | Environmental requirements (operating Temperature/humidity |
| Feature 13 | positive air pressure with respect to the adjoining areas, to help maintain a reduced dust environment for the electronic equipment |
| Feature 14 | Adequate ventilation for medical gas and heat |
| Feature 15 | adequate venting in the event that a superconducting magnet should quench |
| Feature 16 | Floor trenching requirement. |
| ... | ... |
| Feature N | ... |

The validation of a selected site process includes a data integration and storage process 150. The integration and storage system obtains guidelines data from various systems in a standard health interoperability format such as fast healthcare interoperability resources (FHIR). The collected data then undergoes a data aggregation process and a data normalization process. The data aggregation process ensures that all records obtained from different systems and stored at one place ensures that all records obtained from different systems and stored at one place since the interactive design records are stored in multiple systems.

The data normalization process reduces data redundancy and improves data integrity. Data such as equipment layout details, room layout, environment requirements, equipment location and power requirements. The data normalization process makes sure that redundant patient data is removed, and correct data is stored in the storage system.

The output from the AI model 130 is validated against the standard preferred interactive layout design. The interactive layout design and determining the best location of equipment are analysed for their conformance with standard interactive room layouts. A knowledge base includes a master collection of multiple guidelines according to room/floor and equipment's applicability. In general, the parameters of the guidelines that are compared with the output of the model. The comparing includes room layouts (site conditions, application requirements, customer preferences), equipment layouts (equipment configuration, ceiling height, patient table, operator's console); and the knowledgebase (a list of guidelines which provide guidance about managing identified layout design). The comparing solutions are compared with the output from the AI model.

For the optimization of a user routing around the device process, some of the parameters considered for optimizing algorithm are: how many people are needed to be around the device during procedure, time taken for patient to move-in/move-out, option to move-in from multiple sides, etc. The aim of this process is to minimize the flow disruptions caused by placement of the medical device 12 along with the support tools considering the architecture, lighting, heating, and power requirements. The facility layout problem deals with either minimizing the staff effort or improving the overall health environment.

To determine the optimal position for the medical device 12, staff movement must be minimized, and quicker diagnoses and/or treatment should be obtained, while complying with international standards in the placement of the medical device. This can be solved using an adjacency matrix, which defines the acceptability of locating a pair of spaces together for all pairs. If there are n spaces, then the adjacency matrix is of size n×n filled with values $a_{ij}$ denoting the number of edges between 2 spaces i and j. The coefficients are calculated as follows in Equation 3:

$$a_{ij} = \begin{cases} 1 & \text{if } i \text{ and } j \text{ activities are fully adjacent} \\ \alpha & (0.5 \text{ or } 0.75) \text{ if } i \text{ and } j \text{ are partially adjacent} \\ 0 & \text{if } i \text{ and } j \text{ activities are not adjacent} \end{cases}$$

A general layout plan can be generated from the adjacency matrix including initiation of vertices, generation of the position and orientation of a block diagram and scoring the generated block diagram. For the scoring, a total closeness rating (TCR) score is calculated. The TCR rating is helpful in determining the closeness for one space to another. Muther's grid is used for assigning location preference. The preference information is coded into six categories associated with the five vowels, A, E, I, O, and U, plus the letter X, with each meaning:

A Absolutely necessary
E Especially important
I Important
O Okay
U Unimportant
X Undesirable The lower order spaces are scored first. The TCR gives the priority of objects/spaces to be placed next A=absolutely necessary and takes value of 4, E=especially important and takes value of 3, I=important and takes value of 2, O=ordinary closeness and takes value of 1, U=unimportant and takes value of 0, X=undesirable and takes value of −1 or −2 or −3. TCR is the summation of the adjacency coefficient of each row of the adjacency matrix.

Restrictions can affect the insertion process, such as entrance and exits of the facility block, windows permitting day light, HVAC systems, a concrete block which should not be disturbed or not subjected to high shocks, among others.

By allocating the spaces according to the adjacency matrix and the restriction due to various standards, the layout plan is constructed and scored. The layout can be scored according to Equation 4:

$$\text{Layout score} = \sum_{i=1}^{M-1} \sum_{j=i+1}^{M} V(r_{ij}) * a_{ij}$$

where $a_{ij}$ between 0 and 1. Are the adjacency coefficients between activities i and j. $V(r_{ij})$ is the weighing factor for different combination of spaces.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A non-transitory computer readable medium storing instructions executable by at least one electronic processor to perform a method of determining a layout for one or more medical devices in a medical facility, the method comprising:
    obtaining images of a plurality of locations of the medical facility;
    mapping the obtained images to an architectural layout of the medical facility;
    generating a three-dimensional (3D) model of the medical facility based on the mapping;
    determining a recommended location for the one or more medical devices using the 3D model;
    determining a recommended placement of the one or more medical devices in the recommended location based on the recommended location; and
    outputting an image showing the determined recommended placement of the medical devices in the recommended location;
    wherein the determining of the recommended location for the one or more medical devices using the 3D model includes:
    performing a multi-agent optimization in which each agent of the multi-agent optimization optimizes for a corresponding feature selected from one or more of:
        an agent to minimize a distance between the recommended location and an emergency room (ER);
        an agent to minimize a number of elevator trips between the recommended location and the ER; and an agent to minimize a distance between from the recommended location and a nearest emergency exit; and determining the recommended location based on the multi-agent optimization.

2. The non-transitory computer readable medium of claim 1, wherein the obtaining of images of a plurality of locations of the medical facility includes:

obtaining images of interior rooms and hallways of the medical facility with an augmented reality (AR) headset.

3. The non-transitory computer readable medium of claim 2, wherein mapping the obtained images to an architectural layout of the medical facility includes:

receiving, via the AR headset, one or more annotations from a user, the annotations comprising labels of landmarks of the one or more images of the interior rooms and the hallways of the medical facility; and mapping the annotated landmarks to the architectural layout of the medical facility.

4. The non-transitory computer readable medium of claim 2, wherein generating a 3D model of the medical facility based on the mapping includes:

providing, a graphical user interface (GUI), on a display device of the AR headset;

receiving, via at least one user input device of the AR headset, one or more inputs from a user, the inputs being indicative of a labelling or adjustment of landmarks in the obtained images.

5. The non-transitory computer readable medium of claim 4, wherein outputting an image showing the recommended placement for the medical devices includes:

outputting the image of the recommended placement on the display device of the AR headset.

6. The non-transitory computer readable medium of claim 4, wherein outputting the image of the recommended placement on the display device of the AR headset includes:

highlighting portions of the image related to the recommended placement.

7. The non-transitory computer readable medium of claim 1, wherein the obtaining of images of a plurality of locations of the medical facility includes:

obtaining one or more images of an exterior of the medical facility.

8. The non-transitory computer readable medium of claim 1, wherein the multi-agent optimization includes optimizing a weighted average of outputs of the agents of the multi-agent optimization.

9. The non-transitory computer readable medium of claim 1, wherein the outputting of the image showing the determined recommended placement of the medical devices in the recommended location includes:

graphically displaying on the image representations of the optimized agents generated by the performed multi-agent optimization.

10. The non-transitory computer readable medium of claim 1, wherein the determining of the recommended placement for the one or more medical devices based on the determined optimal location includes:

determining a position and/or orientation of the one or more medical devices based on at least building constraints or government constraints of the medical facility.

11. The non-transitory computer readable medium of claim 9, wherein determining of the recommended placement based on at least building constraints or government restraint of the medical facility includes:

using a grid optimization process to identify the position and/or orientation of the one or more medical devices that satisfies the building constraints and government constraints.

12. The non-transitory computer readable medium of claim 1, wherein the determining of the recommended placement for the one or more medical devices based on the determined recommended location includes:

using a machine-learning process trained on historical installations of the one or more medical devices to determine the recommended placement.

13. The non-transitory computer readable medium of claim 1, wherein the method further includes:

validating the recommended location or the recommended placement of the one or more medical devices ensuring that the recommended location or the recommended placement satisfies manufacturing, building, or government regulations related to the medical facility.

14. The non-transitory computer readable medium of claim 13, wherein the validating includes:

repeating the determining of the recommended location or the recommended placement of the one or more medical devices when one or more of the regulations is not satisfied.

15. The non-transitory computer readable medium of claim 1, wherein the method further includes:

determining a recommended placement for a plurality of medical devices.

16. The non-transitory computer readable medium of claim 1, wherein the determining of the recommended placement for the one or more medical devices based on the determined optimal location includes wherein outputting the image of the recommended placement on the display device of the AR headset includes:

outputting the image showing existing medical devices being removed from a location of the medical facility and showing the recommended placement for the one or more medical devices; and determining a location for the removed existing medical devices.

* * * * *